(12) United States Patent
Colegate et al.

(10) Patent No.: US 7,959,931 B2
(45) Date of Patent: Jun. 14, 2011

(54) INFLUENZA VACCINES EXTEMPORANEOUSLY ADSORBED TO ALUMINIUM ADJUVANTS

(75) Inventors: Anthony Colegate, Liverpool (GB); Philip Sizer, Liverpool (GB)

(73) Assignee: Novartis AG, Basel (CH)

( * ) Notice: Subject to any disclaimer, the term of this patent is extended or adjusted under 35 U.S.C. 154(b) by 209 days.

(21) Appl. No.: 12/092,106

(22) PCT Filed: Nov. 6, 2006

(86) PCT No.: PCT/GB2006/004138
§ 371 (c)(1),
(2), (4) Date: Sep. 9, 2008

(87) PCT Pub. No.: WO2007/052060
PCT Pub. Date: May 10, 2007

(65) Prior Publication Data
US 2009/0202590 A1     Aug. 13, 2009

Related U.S. Application Data

(60) Provisional application No. 60/735,605, filed on Nov. 9, 2005.

(30) Foreign Application Priority Data

Nov. 4, 2005 (GB) .................................. 0522601.4

(51) Int. Cl.
*A61K 39/145* (2006.01)

(52) U.S. Cl. ............... 424/209.1; 424/210.1; 424/206.1; 424/278.1

(58) Field of Classification Search .................. None
See application file for complete search history.

(56) References Cited

U.S. PATENT DOCUMENTS 6,372,223 B1 * 4/2002 Kistner et al. ............. 424/209.1
7,238,349 B1 * 7/2007 D'Hondt et al. ............ 424/93.6

FOREIGN PATENT DOCUMENTS

WO     WO 00/15251       3/2000
WO     WO 01/22992    *  4/2001

OTHER PUBLICATIONS

Vanselow et al ( Veterinary Record 117: 37-43, 1985; in IDS).*
Speidel et al (European Journal of Immunology 27:2391-2399, 1997).*
Brady M I et al: "A Surface Antigen Influenza Vaccine Part 2 Pyrogenicity and Antigenicity" Journal of Hygiene, vol. 77, No. 2, 1976, pp. 173-180.
Hehme N et al: "Pandemic preparedness: Lessons learnt from H2N2 and H9N2 candidate vaccines." Medical Microbiology and Immunology, vol. 191, No. 3-4, Dec. 2002, pp. 203-208.
Pressler K et al: "Comparison of the Anti Genicity and Tolerance of an Influenza Aluminum Oxide Adsorbate Vaccine With an Aqueous Vaccine" Pharmatherapeutica, vol. 3, No. 3, 1982, pp. 195-200.
Vanselow B A et al: "Bovine Ephemeral Fever Vaccine Incorporating Adjuvant Quil A: A Comparative Study Using Adjuvants Quil A, Aluminium Hydroxide Gel and Dextran Sulphate" Veterinary Record, British Veterinary Association, London, GB, vol. 117, No. 2, Jul. 13, 1985, pp. 37-43.
Zhang C-H et al: "Immune responses in Balb/c mice induced by a candidate SARS-CoV inactivated vaccine prepared fror F69 strain" Vaccine, Butterworth Scientific, Guildford, GB, vol. 23, No. 24, May 2, 2005, pp. 3196-3201, XP004851707.

* cited by examiner

*Primary Examiner* — Mary E Mosher
(74) *Attorney, Agent, or Firm* — Robert Gorman; Marco Riensche

(57) ABSTRACT

Antigen and adjuvant components of an adjuvanted influenza vaccine are not mixed during manufacture, but are provided as separate components for extemporaneous mixing at the time of use, for example as a kit comprising (i) an antigen component, comprising an influenza virus antigen; and (ii) an adjuvant component, comprising an aluminium salt.

21 Claims, No Drawings

INFLUENZA VACCINES EXTEMPORANEOUSLY ADSORBED TO ALUMINIUM ADJUVANTS

This application is a national stage application of PCT/GB2006/004138 filed Nov. 6, 2006, which claims the benefit of Serial No. GB 0522601.4 filed Nov. 4, 2005 and Ser. No. 60/735,605 filed Nov. 9, 2005. Each of these applications is incorporated herein by reference in its entirety.

GOVERNMENT INTERESTS

This invention was made, in whole or in part, with support from United States Government Contract HHSN266200400032C from the National Institutes of Health/National Institute of Allergy and Infectious Diseases. Accordingly, the United States Government has certain rights in the invention.

All documents cited herein are incorporated by reference in their entirety.

TECHNICAL FIELD

This invention is in the field of adjuvanted vaccines for protecting against influenza virus infection.

BACKGROUND ART

Except for the FLUAD™ product from Chiron Vaccines, which includes an oil-in-water emulsion adjuvant, influenza vaccines currently in general use are unadjuvanted. These vaccines are described in more detail in chapters 17 & 18 of reference 1. They are based on live virus or inactivated virus, and inactivated vaccines can be based on whole virus, 'split' virus or on purified surface antigens (including haemagglutinin and neuraminidase).

More recently, the inclusion of aluminium salt adjuvants has been suggested for influenza vaccines (e.g. see references 2-5). As well as requiring extra mixing steps during manufacture, thereby slowing down overall manufacture, inclusion of these salts is associated with various problems. For example, their insolubility means that adsorbed antigens settle from suspension, so preparation of individual doses from bulk vaccine requires extra care. In addition, binding of antigen to the salts complicates quality control of the final vaccines. In particular, some potency tests for influenza vaccines are based on in vitro immunoassays that require unbound antigen i.e. adsorption to the adjuvant means that these tests cannot be used.

It is an object of the invention to provide further and improved adjuvanted influenza vaccines (for both pandemic and interpandemic use) and methods for their preparation.

DISCLOSURE OF THE INVENTION

According to the invention, the antigen and adjuvant components of an adjuvanted influenza vaccine are not mixed during manufacture, but are provided as separate components for extemporaneous mixing at the time of use. The invention is effective only because it has been found (see examples herein) that adsorption of the antigen to the adjuvant occurs substantially instantaneously, and is irreversible under the conditions experienced during vaccination. Thus the invention avoids the various problems that arise from performing the mixing during manufacture.

Therefore the invention provides a kit comprising: (i) an antigen component, comprising an influenza virus antigen; and (ii) an adjuvant component, comprising an aluminium salt. Component (i) does not include an aluminium salt adjuvant, and component (ii) does not include an influenza virus antigen.

The invention also provides (i) an antigen component comprising an influenza virus antigen, and (ii) an adjuvant component comprising an aluminium salt, for simultaneous separate or sequential use.

The invention also provides an immunogenic composition, comprising an influenza virus antigen and an aluminium salt adjuvant, wherein the composition was prepared by extemporaneous mixing of the antigen and adjuvant at the point of use.

The invention also provides a process for preparing an influenza vaccine, comprising the steps of: (i) preparing an antigen component comprising an influenza virus antigen; (ii) preparing an adjuvant component comprising an aluminium salt; and (iii) combining the antigen and adjuvant components into a kit. The process may also provide the step of (iv) mixing the antigen and adjuvant components for administration to a patient, but step (iv) will typically be performed by a healthcare professional at the time of use, rather than by a manufacturer.

The invention also provides a process for preparing and administering an influenza vaccine, comprising the steps of: (i) mixing the components of a kit that comprises an antigen component comprising an influenza virus antigen and an adjuvant component comprising an aluminium salt; and (ii) administering the mixed components to a patient. This process will typically involve: shaking the adjuvant component to disperse any settled aluminium salts; aseptically adding the antigen component to the adjuvant component; inverting or gently shaking the mixed components; withdrawing the mixed components into a syringe; and administering the mixed components to the patient. Administration to a patient will typically take place less than 24 hours (e.g. $\leq 18$ hours, $\leq 12$ hours, $\leq 6$ hours, $\leq 3$ hours, $\leq 2$ hours, $\leq 1$ hour, $\leq 30$ minutes, $\leq 20$ minutes, $\leq 10$ minutes, $\leq 5$ minutes, $\leq 2$ minutes, $\leq 1$ minute, etc.) after the mixing.

The Kit

Kits of the invention comprise two components: one with antigen and one with adjuvant. These two components are kept separately in a kit until it is decided to prepare a vaccine for administration to a patient, at which point the components are mixed to give a vaccine in which the antigen is adsorbed to the adjuvant.

The two components are thus physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The pre-filled syringe can be used (e.g. with a needle) to insert its contents into the second container for mixing, and the mixture can then be withdrawn into the syringe. The mixed contents of the syringe can then be administered to a patient, typically through a new sterile needle. Packing one component in a pre-filled syringe thus eliminates the need for using a separate syringe for patient administration.

In another preferred arrangement, the two kit components are held together but separately in the same syringe e.g. a dual-chamber syringe, such as those disclosed in references 6-13 etc. When the syringe is actuated (e.g. during administration to a patient) then the contents of the two chambers are mixed. This arrangement avoids the need for a separate mixing step at the time of use. The contents of the two chambers will generally both be in aqueous form.

In some arrangements, one of the components (typically the antigen component rather than the adjuvant component) is in dry form (e.g. in a lyophilised form), with the other component being in aqueous form. The two components can be mixed in order to reactivate the dry component and give an aqueous composition for administration to a patient. In other less preferred arrangements, both components are in dry form. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc.

One preferred arrangement uses an aqueous adjuvant component in a pre-filled syringe and a lyophilised antigen component in a vial.

Where both components are aqueous, they may be mixed at various volume ratios e.g. between 1:5 (excess volume of aqueous antigen) and 5:1 (excess volume of aqueous adjuvant). A ratio of between 1:2 and 2:1 is preferred e.g. about 1:1.

Suitable containers for kits include vials and disposable syringes. These containers should be sterile.

Where a component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

Influenza vaccines are typically administered in a dosage volume of about 0.5 ml, although a half dose (i.e. about 0.25 ml) may be administered to children. Containers may be marked to show a half-dose volume, to facilitate the delivery of a half-dose to children e.g. a syringe containing a 0.5 ml dose may have a mark showing a 0.25 ml volume.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Where a glass container (e.g. a syringe or a vial) is used, then it is preferred to use a container made from a borosilicate glass rather than from a soda lime glass.

The kit may include (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

The kit is preferably stored at between 2° C. and 8° C. It should not be frozen.

The Influenza Virus Antigen

One of the kit components contains influenza virus antigen. These antigens will typically be prepared from influenza virions but, as an alternative, antigens such as haemagglutinin can be expressed in a recombinant host (e.g. in an insect cell line using a baculovirus vector) and used in purified form [14,15]. In general, however, antigens will be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virus, split virus, or purified surface antigens (including haemagglutinin and, usually, also including neuraminidase).

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split viruses are obtained by treating virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 16-21, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Influenza proteins other than HA and NA can also be used as the influenza antigen, including fragments of natural proteins. Combinations thereof can also be used.

Influenza antigens can also be presented in the form of virosomes [22].

The influenza virus may be attenuated. The influenza virus may be temperature-sensitive. The influenza virus may be cold-adapted. These three possibilities apply in particular for live viruses.

Influenza virus strains for use in vaccines change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16.

The adjuvanted compositions of the invention are particularly useful for immunizing against pandemic strains. The characteristics of an influenza strain that give it the potential to cause a pandemic outbreak are: (a) it contains a new haemagglutinin compared to the haemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's haemagglutinin; (b) it is capable of being transmitted horizontally in the human population; and (c) it is pathogenic to humans. A virus with H5 haemagglutinin type is preferred for immunising against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3 [23], with clades 1 and 3 being particularly relevant.

Other strains that can usefully be included in the compositions are strains which are resistant to antiviral therapy (e.g. resistant to oseltamivir [24] and/or zanamivir), including resistant pandemic strains [25].

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is preferred, including antigens from two influenza A virus strains and one influenza B virus strain, although monovalent vaccines are also useful (e.g. for pandemic strains).

The influenza virus may be a reassortant strain, and may have been obtained by reverse genetics techniques. Reverse genetics techniques [e.g. 26-30] allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [31-33], and these methods will also involve the use of plasmids to express all or some (e.g. just the PB1, PB2, PA and NP proteins) of the viral proteins, with 12 plasmids being used in some methods.

To reduce the number of plasmids needed, a recent approach [34] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 34 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [35]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [36,37].

Thus a virus (in particular an influenza A virus) may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g.

in a human) influenza virus. It may include a NS segment that originated in an avian influenza virus.

The viruses used as the source of the antigens can be grown either on SPF eggs or on cell culture. The current standard method for influenza virus growth uses embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus [18].

The cell substrate will typically be a mammalian cell line. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line.

Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. The use of mammalian cells means that vaccines can be free from chicken DNA, as well as being free from egg proteins (such as ovalbumin and ovomucoid), thereby reducing allergenicity.

Preferred mammalian cell lines for growing influenza viruses include: MDCK cells [38-41], derived from Madin Darby canine kidney; Vero cells [42-44], derived from African green monkey (Cercopithecus aethiops) kidney; or PER.C6 cells [45], derived from human embryonic retinoblasts. These cell lines are widely available e.g. from the American Type Cell Culture (ATCC) collection [46], from the Coriell Cell Repositories [47], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 4850], including cell lines derived from ducks (e.g. duck retina) or hens e.g. chicken embryo fibroblasts (CEF), etc. Examples include avian embryonic stem cells [48, 51], including the EBx cell line derived from chicken embryonic stem cells, EB45, EB14, and EB14-074 [52].

The most preferred cell lines for growing influenza viruses are MDCK cell lines. The original MDCK cell line is available from the ATCC as CCL-34, but derivatives of this cell line may also be used. For instance, reference 38 discloses a MDCK cell line that was adapted for growth in suspension culture ('MDCK 33016', deposited as DSM ACC 2219). Similarly, reference 53 discloses a MDCK-derived cell line that grows in suspension in serum-free culture ('B-702', deposited as FERM BP-7449). Reference 54 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 55 discloses MDCK cell lines with high susceptibility to infection, including 'MDCK.5F1' cells (ATCC CRL-12042). Any of these MDCK cell lines can be used.

Where virus has been grown on a mammalian cell line then the antigen component in the kit will advantageously be free from egg proteins (e.g. ovalbumin and ovomucoid) and from chicken DNA, thereby reducing allergenicity.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [56]. Absence of herpes simplex viruses is particularly preferred.

Where virus has been grown on a cell line then the antigen component preferably contains less than 10 ng (preferably less than 1 ng, and more preferably less than 100 pg) of residual host cell DNA per dose, although trace amounts of host cell DNA may be present. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 57 & 58, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [59].

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 pg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

For growth on a cell line, such as on MDCK cells, virus may be grown on cells in suspension [38,60 61] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [62] (e.g. 30-36° C., or at about 30° C., 31° C., 32° C., 33° C., 34° C., 35° C., 36° C.), for example during viral replication.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffusion (SRID) assay. Vaccines typically contain about 15 µg of HA per strain, although lower doses are also used e.g. for children, or in pandemic situations. Fractional doses such as ½ (i.e. 7.5 µg HA per strain), ¼ and ⅛ have been used [4,5], as have higher doses (e.g. 3× or 9× doses [63,64]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 1.9, about 1.5, etc. per strain. These lower doses are most useful when an adjuvant is present in the vaccine, as with the invention.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g. hyperbasic regions around the cleavage site between HA1 and HA2) that cause a virus to be highly pathogenic in avian species, as these determinants can otherwise prevent a virus from being grown in eggs.

The antigen component of the kits of the invention may include detergent e.g. a polyoxyethylene sorbitan ester surfactant (known as the 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10, α-tocopheryl hydrogen succinate and polysorbate 80. Other residual components in trace amounts could be antibiotics (e.g. neomycin, kanamycin, polymyxin B).

An inactivated but non-whole cell vaccine (e.g. a split virus vaccine or a purified surface antigen vaccine) may include matrix protein, in order to benefit from the additional T cell epitopes that are located within this antigen. Thus a non-whole cell vaccine (particularly a split vaccine) that includes haemagglutinin and neuraminidase may additionally include M1 and/or M2 matrix protein. Where a matrix protein is present, inclusion of detectable levels of M2 matrix protein, or a fragment of M1 protein, is preferred. Nucleoprotein may also be present.

The Adjuvant

Adjuvants that have been used in influenza vaccines include chitosan [65], oil-in-water emulsions such as MF59 [66], water-in-oil-in-water emulsions [67], aluminium salts [2,5], CpG oligodeoxynucleotides such as CpG 7909 [68], *E. coli* heat labile toxin [69,87] and its detoxified mutants [70-71], monophosphoryl lipid A [72] and its 3-o-deacylated derivative [73], pertussis toxin mutants [74], muramyl dipeptides [75], etc.

According to the invention, however, the adjuvant component is based on aluminium salts. These salts include the adjuvants known as aluminium hydroxide and aluminium phosphate. These names are conventional, but are used for convenience only, as neither is a precise description of the actual chemical compound which is present [e.g. see chapter 9 of reference 76]. The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of ref. 76]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of ref. 76].

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment of the invention, the adjuvant component includes a mixture of both an aluminium hydroxide and an aluminium phosphate [4]. In this case there may be more aluminium phosphate than hydroxide e.g. a weight ratio of at least 2:1 e.g. $\geq 5:1$, $\geq 6:1$, $\geq 7:1$, $\geq 8:1$, $\geq 9:1$, etc.

The concentration of $Al^{+++}$ in a composition for administration to a patient is preferably less than 10 mg/ml e.g. $\leq 5$ mg/ml, $\leq 4$ mg/ml, $\leq 3$ mg/ml, $\leq 2$ m/ml, $\leq 1$ mg/ml, etc. A preferred range is between 0.3 and 1 mg/ml. A maximum of <0.85 mg/dose is preferred.

As well as including one or more aluminium salt adjuvants, the adjuvant component may include one or more further adjuvant or immunostimulating agents. Such additional components include, but are not limited to: a 3-O-deacylated monophosphoryl lipid A adjuvant ('3d-MPL'); and/or an oil-in-water emulsion. 3d-MPL has also been referred to as 3 de-O-acylated monophosphoryl lipid A or as 3-O-desacyl-4'-monophosphoryl lipid A. The name indicates that position 3 of the reducing end glucosamine in monophosphoryl lipid A is de-acylated. It has been prepared from a heptoseless mutant of S. minnesota, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF. Preparation of 3d-MPL was originally described in reference 77, and the product has been manufactured and sold by Corixa Corporation under the trade name MPL™. Further details can be found in refs 78 to 81.

Finally, in alternative embodiments of the invention, a calcium salt is used instead of an aluminium salt. In these embodiments, the adjuvant component will typically include a calcium phosphate salt.

Pharmaceutical Compositions

The antigen component and the adjuvant component of the kit will both be pharmaceutically acceptable, as will the product of their mixing. The mixed product may include components in addition to the antigen and adjuvant, and these may originate from the antigen component and/or the adjuvant component and/or an optional third component.

Thus the final mixture will typically include one or more pharmaceutical carrier(s) and/or excipient(s). A thorough discussion of such carriers and excipients is available in reference 82.

The final mixture may include preservatives such as thiomersal or 2-phenoxyethanol. It is preferred, however, that the vaccine should be substantially free from (i.e. less than 5 µg/ml) mercurial material e.g. thiomersal-free [17,83]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

The composition may include citrate ions.

Compositions for administration will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [84], but keeping osmolality in this range is nevertheless preferred.

Compositions for administration may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition for administration will generally be between 5.0 and 8.1, and more typically between 6.0 and 8.0, or between 6.5 and 7.5, or between 7.0 and 7.8. The process of the invention may therefore include a step of adjusting the pH of the bulk vaccine prior to packaging.

Individual kit components, including containers, are preferably sterile.

Kit components are preferably non-pyrogenic e.g. containing <1 EU (endotoxin unit, a standard measure) per dose, and preferably <0.1 EU per dose.

Kit components are preferably gluten free.

The kit components may include material for a single immunisation, or may include material for multiple immunisations (i.e. a 'multidose' kit). Thus, for example, antigen for 10 doses could be included in one container, adjuvant for 10 doses in a second container. The two components could by mixed in a surgery on the morning of use to provide 10 doses for administration to a series of patients during the day. Each dose would be withdrawn into a fresh syringe for administration. The inclusion of a preservative is preferred in multidose arrangements. As an alternative (or in addition) to including a preservative in multidose compositions, the compositions may be contained in a container having an aseptic adaptor for removal of material.

Methods of Treatment and Administration of the Vaccine

After mixing, compositions of the invention are suitable for administration to human patients, and the invention provides a method of raising an immune response in a patient, comprising the step of administering a composition of the invention to the patient.

The invention also provides a kit or composition of the invention for use as a medicament.

The invention also provides the use of (i) an influenza virus antigen and (ii) an adjuvant component comprising an aluminium salt, in the manufacture of a medicament for raising an immune response in a patient, wherein the medicament comprises the antigen and adjuvant as separate components.

The immune response raised by these methods and uses will generally include an antibody response, preferably a protective antibody response. Methods for assessing antibody responses, neutralising capability and protection after influenza virus vaccination are well known in the art. Human studies have shown that antibody titres against haemagglutinin of human influenza virus are correlated with protection (a serum sample haemagglutination-inhibition titre of about 30-40 gives around 50% protection from infection by a homologous virus) [85]. Antibody responses are typically measured by haemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [86-88], oral [89], intradermal [90,91], transcutaneous, transdermal [92], etc.

Vaccines prepared according to the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. $\geq 50$ years old, $\geq 60$ years old, and preferably $\geq 65$ years), the young (e.g. $\leq 5$ years old), hospitalised patients, healthcare workers, armed service and military personnel, pregnant women, the chronically ill, immunodeficient patients, patients who have taken an antiviral compound (e.g. an oseltamivir or zanamivir compound, such as oseltamivir phosphate—see below) in the 7 days prior to receiving the vaccine, people with egg allergies and people traveling abroad. The vaccines are not suitable solely for these groups, however, and may be used more generally in a population. For pandemic strains, administration to all age groups is preferred.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir). These antivirals include neuraminidase inhibitors, such as a (3R,4R,5S)-4-acetylamino-5-amino-3(1-ethylpropoxy)-1-cyclohexene-1-carboxylic acid, including esters thereof (e.g. the ethyl ester) and salts thereof (e.g. the phosphate salt). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

Treatment can be by a single dose schedule or a multiple dose schedule. Multiple doses may be used in a primary immunisation schedule and/or in a booster immunisation schedule. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

As compositions and kits of the invention include an aluminium-based adjuvant, settling of components may occur during storage. The composition should therefore be shaken prior to administration to a patient. The shaken composition will be a turbid white suspension.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a cell substrate is used for reassortment or reverse genetics procedures, it is preferably one that has been approved for use in human vaccine production e.g. as in Ph Eur general chapter 5.2.3.

MODES FOR CARRYING OUT THE INVENTION

Because of the above-mentioned problems associated with the use of aluminium salts for adjuvanting influenza virus vaccines, it was decided to investigate if vaccines could be prepared in which the adjuvant and antigen components are kept apart until the time of use, but in which antigen adsorption can still take place. To determine the feasibility of this approach, purified surface antigens from an influenza virus were mixed with aluminium hydroxide suspensions. Immediately following mixture, the aluminium salt was sedimented by bench centrifugation and the amount of protein remaining in the supernatant (i.e. the amount of unadsorbed protein) was measured.

Current Influenza A Virus Strains

Haemagglutinin was purified from influenza virus A/New Caledonian (H1N1) or A/Wyoming (H3N2), and was diluted to give 75 μg HA/ml. An aluminium hydroxide adjuvant was prepared at 4.25 mg/ml (approximately 1.5 mg $Al^{+++}$/ml). 1 ml of the adjuvant suspension was added to 4 ml of the antigen solution in a 15 ml Falcon tube, and the mixture was inverted and incubated at room temperature. Samples were taken at time zero and then at 5, 10, 20, 30, 60, 90 and 120 minutes. Controls were the antigen alone (10 mM PBS, pH 7.7) or the adjuvant alone (10 mM PBS, pH 7.7). Samples were immediately centrifuged at 400 rpm to sediment the adsorbed material for analysis. Protein content was assessed by BioRad™ protein assay and by non-denaturing SDS-PAGE.

The results of the adsorption study for the two strains were as follows, normalised to 100% being the protein content of the antigen-only control:

| Sample | A/New Caledonia Protein in supernatant | A/Wyoming Protein in supernatant |
|---|---|---|
| Antigen control | 100 | 100 |
| Adjuvant control | 0.0 | 0.3 |
| 0 minutes | 3.8 | 1.2 |
| 5 minutes | 1.7 | 0.7 |
| 10 minutes | 2.2 | 0.6 |
| 20 minutes | 2.2 | 0.6 |
| 30 minutes | 1.6 | 0.8 |
| 60 minutes | 1.4 | 0.5 |
| 90 minutes | 1.8 | 0.5 |
| 120 minutes | 1.9 | 0.5 |

Thus a high degree of adsorption occurs very rapidly. The differences at the various time points were not significant. To confirm the results, SYPRO ruby dye staining was used on SDS-PAGE separations of the supernatants. No protein bands were visible in the adjuvant control, 0, 5, 10, 20 or 30 minute samples. Thus any protein present was below the limit of detection by this method, which is sensitive enough to detect 1-2 ng of protein.

Results showed that at least 97% of the antigen rapidly became adsorbed to the adjuvant. Surprisingly, adsorption occurs essentially instantaneously, which would permit an adjuvanted influenza vaccine to be distributed without pre-adsorption to the adjuvant. Thus an adjuvant vaccine can be prepared more rapidly, which will be most useful in a pandemic situation. These results have been achieved with two different strains of influenza A virus, and it is fully expected that the same effect will be seen with other strains and with other adjuvants based on insoluble aluminium salts.

Pandemic Influenza A Strain

A purified surface antigen formulation of A/Vietnam/1203/2004 x A/PR/8/34 (H5N1) influenza virus 2:6 reassortant was prepared. The haemagglutinin content was estimated to be 41 µg HA/mL as determined by SRID. 30 mL A/H5N1 was concentrated using the Ultrafree-15 centrifugal filter device to approximately 15 mL. The total protein content of both the original and concentrated A/H5N1 was determined by the Bio-Rad protein assay with a 0-50 µg/mL gamma globulin standard curve. Using this result, the proportion of HA to total protein was calculated. This value was then used to calculate the final volume required for a 60 µg HA/mL solution of A/H5N1.

0.7 mL of a 2 mg/mL aluminium hydroxide adjuvant was added to 0.7 mL of 60 µg HA/mL MBP in a 1.5 mL microcentrifuge tube. The solutions were mixed by inversion and incubated at room temperature (approximately 20° C.). Duplicate samples were taken at 5 minutes, 10 minutes, 30 minutes, 2 hours, 8 hours and 24 hours. Controls were 0.7 mL 10 mM PBS, pH 7.7 added to 0.7 mL 60 µg HA/mL MBP and 0.7 mL 10 mM PBS, pH 7.7 added to 0.7 mL 2 mg/mL aluminium hydroxide. Samples were centrifuged at 13000 rpm for 1 minute at room temperature, to remove the suspended aluminium hydroxide, and the supernatant decanted into a labelled 7 mL sterile bijou. Results were analysed as described above by BioRad™ protein assay and by non-denaturing SDS-PAGE with SYPRO dye, and were as follows.

| Sample | Protein in supernatant |
|---|---|
| Antigen control | 100 |
| Adjuvant control | 0.5 |
| 5 minutes | 3.7 |
| 10 minutes | 2.1 |
| 30 minutes | 0.2 |
| 2 hours | 0.3 |
| 8 hours | 1.1 |
| 24 hours | 2.4 |

The results for the A/H5N1 formulation were comparable to the experiments conducted using the equivalent A/New Caledonia and A/Wyoming preparations. Very low levels of protein were detected in the supernatant for all samples using the Bio-Rad protein assay, confirming that almost all the protein remained bound to the aluminium hydroxide pellet. Sensitive SYPRO ruby dye staining of the samples after SDS-PAGE separation revealed no protein bands in the adjuvant control or in any of the six timed samples. Thus any protein present was below the limit of detection by this method. There was no significant difference between the protein concentrations at any of the time points. All sample absorbencies and subsequent protein concentration estimations for the aluminium hydroxide control and timed samples were below the lower limit of the 5 to 50 µg/mL standard curve.

Thus the data indicate that A/H5N1 protein is instantaneously adsorbed to the aluminium salt adjuvant and remains stably attached for at least 24 hours.

Human Clinical Data

As reported in reference 93, 300 volunteers in a randomised open-label non-controlled phase I trial received one of six inactivated monovalent split influenza A/Vietnam/1194/2004 (H5N1) vaccine formulations, comprising 3 different doses of HA (7.5 µg, 15 µg or 30 µg) with or without aluminium hydroxide adjuvant. Individuals received two vaccinations, and blood samples were analysed by haemagglutination inhibition and microneutralisation.

The vaccine was produced in embryonated chicken eggs, using the licensed manufacturing process used for the VAXIGRIP™ interpandemic vaccine [94]. The vaccine strain was the influenza A/Vietnam/1194/2004/NIBRG14 (H5N1) reference strain prepared by the NIBSC. This strain contains modified haemagglutinin and neuraminidase from the highly pathogenic avian strain influenza A/Vietnam/1194/2004 and other viral proteins from influenza A/PR/8/34 (H1N1). The haemagglutinin was modified to remove the multibasic amino acid sequence at the cleavage site.

0.5 ml syringes (23 gauge, 1 inch needle) were filled with the split vaccine at a level of 7·5 µg, 15 µg, or 30 µg of haemagglutinin, in a phosphate buffered saline solution without adjuvant. For unadjuvanted vaccination, these syringes were used in patients directly. For adjuvanted vaccination, however, the contents of a syringe were injected into a sterile vial, as were the contents of a syringe containing aluminium hydroxide adjuvant. This mixing took place by the bedside, just before use, and after 10 seconds of mixing the contents were drawn into a new syringe (23 gauge, 1 inch needle), with gentle swirling to homogenise the antigen/adjuvant suspension, and then injected into patients intramuscularly (deltoid). Injection volume was 0.5 ml, except for the adjuvanted 30 µg formulation (1 ml volume). The final adjuvant content of vaccines was 600 µg. Preliminary studies of mixing antigen and adjuvant had shown similar adsorption coefficients for all three antigen doses.

Each participant received two intramuscular injections, 21 days apart (days 0 & 21). Blood samples were taken on days 0, 21 and 42.

All six formulations were well tolerated with no reports of serious adverse events between days 0 and 42, no severe injection-site pain, and no febrile episodes with an oral temperature of more than 38° C.

All formulations induced an immune response, with responses detectable in some individuals after only one dose. With respect to haemagglutinin inhibition, between 6% and 34% of each group had titres of 32 or more on day 21, the proportion increasing to 28-67% on day 42. Neutralising antibody responses followed a similar pattern to those of haemagglutinin inhibition. The adjuvanted 30 µg formulation induced the greatest response (67% haemagglutinin-inhibition seroconversion rate after two vaccinations). In particular, a two-dose regimen with the adjuvanted 30 µg H5N1 vaccine showed an immune response consistent with European regulatory requirements for licensure of seasonal influenza vaccines.

It will be understood that the invention has been described by way of example only and modifications may be made whilst remaining within the scope and spirit of the invention.

REFERENCES

The Contents of Which are Hereby Incorporated by Reference

[1] *Vaccines*. (eds. Plotkin & Orenstein). 4th edition, 2004, ISBN: 0-7216-9688-0.
[2] U.S. Pat. No. 6,372,223.
[3] WO00/15251.
[4] WO01/22992.
[5] Hehme et al. (2004) *Virus Res.* 103(1-2):163-71.
[6] WO2005/089837.
[7] U.S. Pat. No. 6,692,468.
[8] WO00/07647.
[9] WO99/17820.
[10] U.S. Pat. No. 5,971,953.
[11] U.S. Pat. No. 4,060,082.
[12] EP-A-0520618.
[13] WO98/01174.
[14] WO96/37624.
[15] WO98/46262.
[16] WO02/28422.
[17] WO02/097072.
[18] WO2005/113756.
[19] WO02/067983.
[20] WO02/074336.
[21] WO01/21151.
[22] Huckriede et al. (2003) *Methods Enzymol* 373:74-91.
[23] World Health Organisation (2005) *Emerging Infectious Diseases* 11(10): 1515-21.
[24] Herlocher et al. (2004) *J Infect Dis* 190(9):1627-30.
[25] Le et al. (2005) *Nature* 437(7062):1108.
[26] Hoffmann et al. (2002) *Vaccine* 20:3165-3170.
[27] Subbarao et al. (2003) *Virology* 305:192-200.
[28] Liu et al. (2003) *Virology* 314:580-590.
[29] Ozaki et al. (2004) *J. Virol.* 78:1851-1857.
[30] Webby et al. (2004) *Lancet* 363:1099-1103.
[31] WO00/60050.
[32] WO01/04333.
[33] U.S. Pat. No. 6,649,372.
[34] Neumann et al. (2005) *Proc Natl Acad Sci USA* 102: 16825-9.
[35] WO2006/067211.
[36] WO01/83794.
[37] Hoffmann et al. (2000) *Virology* 267(2):310-7.
[38] WO97/37000.
[39] Brands et al. (1999) *Dev Biol Stand* 98:93-100.
[40] Halperin et al. (2002) *Vaccine* 20:1240-7.
[41] Tree et al. (2001) *Vaccine* 19:3444-50.
[42] Kistner et al. (1998) *Vaccine* 16:960-8.
[43] Kistner et al. (1999) *Dev Biol Stand* 98: 101-110.
[44] Bruhl et al. (2000) *Vaccine* 19:1149-58.
[45] Pau et al. (2001) *Vaccine* 19:2716-21.
[46] http://www.atcc.org/
[47] http://locus.umdnj.edu/
[48] WO03/076601.
[49] WO2005/042728.
[50] WO03/043415.
[51] WO01/85938.
[52] WO2006/108846.
[53] EP-A-1260581 (WO01/64846).
[54] WO2006/071563.
[55] WO2005/113758.
[56] WO2006/027698.
[57] EP-B-0870508.
[58] U.S. Pat. No. 5,948,410.
[59] International patent application entitled "CELL-DERIVED VIRAL VACCINES WITH LOW LEVELS OF RESIDUAL CELL DNA", filed 1 Nov. 2006 claiming priority US-60/732,786.
[60] WO03/023021
[61] WO03/023025.
[62] WO97/37001.
[63] Treanor et al. (1996) *J Infect Dis* 173:1467-70.
[64] Keitel et al. (1996) *Clin Diagn Lab Immunol* 3:507-10.
[65] U.S. Pat. No. 6,534,065.
[66] Frey et al. (2003) *Vaccine* 21:4234-7.
[67] Bozkir & Hayta (2004) *Drug Target* 12:157-64.
[68] Cooper et al. (2004) *Vaccine* 22:3136-43.
[69] Guebre-Xabier et al. (2003) *J Virol* 77:5218-25.
[70] Peppoloni et al. (2003) *Expert Rev Vaccines* 2:285-93.
[71] Pine et al. (2002) *J Control Release* 85:263-70.
[72] Baldridge et al. (2000) *Vaccine* 18:2416-25.
[73] WO94/19013.
[74] EP-A-0721782.
[75] U.S. Pat. No. 5,292,506.
[76] *Vaccine Design: The Subunit and Adjuvant Approach* (eds. Powell & Newman) Plenum Press 1995 (ISBN 0-306-44867-X).
[77] UK patent application GB-A-2220211.
[78] Myers et al. (1990) pages 145-156 of *Cellular and molecular aspects of endotoxin reactions.*
[79] Ulrich (2000) Chapter 16 (pages 273-282) of *Vaccine Design . . .* (1995) eds. Powell & Newman. ISBN: 030644867X.
[80] Johnson et al. (1999) *J Med Chem* 42:4640-9.
[81] Baldrick et al. (2002) *Regulatory Toxicol Pharmacol* 35:398-413.
[82] Gennaro (2000) *Remington: The Science and Practice of Pharmacy.* 20th edition, ISBN: 0683306472.
[83] Banzhoff (2000) *Immunology Letters* 71:91-96.
[84] Nony et al. (2001) *Vaccine* 27:3645-51.
[85] Potter& Oxford (1979) *Br Med Bull* 35: 69-75.
[86] Greenbaum et al. (2004) *Vaccine* 22:2566-77.
[87] Zurbriggen et al. (2003) *Expert Rev Vaccines* 2:295-304.
[88] Piascik (2003) *J Am Pharm Assoc* (Wash D.C.). 43:728-30.
[89] Mann et al. (2004) *Vaccine* 22:2425-9.
[90] Halperin et al. (1979) *Am J Public Health* 69:1247-50.
[91] Herbert et al. (1979) *J Infect Dis* 140:234-8.

[92] Chen et al. (2003) *Vaccine* 21:2830-6.
[93] Bresson et al. (2006) *Lancet*. DOI:10.1016/S0140-6736(06)68656-X.
[94] Lina et al. (2000) *Biologicals* 28:95-103.

The invention claimed is:

1. A kit comprising: (i) an antigen component, comprising an influenza virus antigen; and (ii) an adjuvant component, comprising an aluminium salt, wherein the adjuvant component is not mixed with any influenza virus antigens.

2. The kit of claim 1, wherein one or both of the components is/are in a vial.

3. The kit of claim 1, wherein one or both of the components is/are in a syringe.

4. The kit of claim 1, wherein one of the components is in a syringe and the other component is in a vial.

5. The kit of claim 4, wherein the antigen component is in a syringe.

6. The kit of claim 1, where the influenza virus antigen is inactivated virus.

7. The kit of claim 6, wherein the influenza virus antigen comprises whole virus, split virus, or purified surface antigens.

8. The kit of claim 1, where the influenza virus antigen is from a H1, H2, H3, H5, H7 or H9 influenza A virus subtype.

9. The kit of claim 1, where the influenza virus antigen is prepared from an influenza virus grown on eggs.

10. The kit of claim 1, where the influenza virus antigen is prepared from an influenza virus grown on cell culture.

11. The kit of claim 10, where the influenza virus antigen component is free from ovalbumin, ovomucoid and chicken DNA.

12. The kit of claim 10, where the influenza virus antigen component contains less than 10 ng of cellular DNA from the cell culture host.

13. The kit of claim 1, where the influenza virus antigen component contains between 0.1 and 50 μg of haemagglutinin per viral strain in the component.

14. The kit of claim 1, where the adjuvant component includes an aluminium hydroxide adjuvant.

15. The kit of claim 1, where the adjuvant component includes an aluminium phosphate adjuvant.

16. A process for preparing an influenza vaccine, comprising the steps of: (i) preparing an antigen component comprising an influenza virus antigen; (ii) preparing an adjuvant component comprising an aluminium salt, wherein the adjuvant component is not mixed with any influenza virus antigens; and (iii) combining the antigen and adjuvant components into a kit.

17. A process for preparing and administering an influenza vaccine, comprising the steps of: (i) mixing the components of the kit of claim 1; and (ii) administering the mixed components to a patient.

18. A process for preparing and administering an influenza vaccine, comprising the steps of: (a) combining (i) an antigen component comprising an influenza virus antigen and (ii) an adjuvant component comprising an aluminium salt; and (b) administering the vaccine to a patient within 12 hours of performing step (a).

19. The kit of claim 1, wherein the antigen component and the adjuvant component are formulated for administration within ten minutes of mixing.

20. The process of claim 17, wherein step (ii) comprises administering the mixed components to a patient within ten minutes of mixing the components.

21. The process of claim 18, wherein step (b) comprises administering the vaccine to a patient within 10 minutes of performing step (a).

* * * * *